United States Patent [19]

Regan

[11] Patent Number: 5,307,953
[45] Date of Patent: May 3, 1994

[54] SINGLE DOSE DISPENSER HAVING A PIERCING MEMBER

[75] Inventor: Philip M. Regan, Ware, Great Britain

[73] Assignee: Glaxo Group Limited, Middlesex, United Kingdom

[21] Appl. No.: 984,913

[22] Filed: Dec. 2, 1992

[30] Foreign Application Priority Data

Dec. 3, 1991 [GB] United Kingdom ............. 9125699

[51] Int. Cl.⁵ .............................................. B67D 5/00
[52] U.S. Cl. ............................... 222/82; 222/83; 604/203
[58] Field of Search ................ 222/82, 83, 383, 385, 222/402.1; 604/200, 201, 204, 214, 203; 239/309

[56] References Cited

U.S. PATENT DOCUMENTS

| | | | |
|---|---|---|---|
| 3,412,900 | 11/1968 | Macaulay | 222/82 |
| 3,512,524 | 5/1970 | Drewe | 604/204 |
| 3,845,763 | 11/1974 | Cloyd | 604/203 |
| 3,856,185 | 12/1974 | Riccio | 222/193 |
| 3,884,229 | 5/1975 | Raines et al. | 604/209 |
| 3,916,894 | 11/1975 | Cloyd | 604/203 |
| 4,017,007 | 4/1977 | Riccio | 222/80 |
| 4,131,217 | 12/1978 | Sandegren | 222/82 |
| 4,203,443 | 5/1980 | Genese | 222/83 |
| 4,344,573 | 8/1982 | De Felice | 239/320 |
| 4,445,895 | 5/1984 | Margulies | 604/201 |
| 4,757,916 | 7/1988 | Goncalves | 222/83 |
| 4,921,142 | 5/1990 | Graf et al. | 222/162 |
| 4,946,069 | 8/1990 | Fuchs | 222/43 |
| 4,962,868 | 10/1990 | Borchard | 222/49 |

FOREIGN PATENT DOCUMENTS

| | | |
|---|---|---|
| 2020425 | 1/1991 | Canada . |
| 0218840 | 4/1987 | European Pat. Off. . |
| 0272035 | 6/1988 | European Pat. Off. . |
| 0282338 | 9/1988 | European Pat. Off. . |
| 0311863 | 4/1989 | European Pat. Off. . |
| 0388651 | 9/1990 | European Pat. Off. . |
| 0407276 | 1/1991 | European Pat. Off. . |
| 0452728 | 10/1991 | European Pat. Off. . |
| 0486894 | 5/1992 | European Pat. Off. . |
| 3631341 | 4/1987 | Fed. Rep. of Germany . |
| 88/01881 | 3/1988 | PCT Int'l Appl. . |
| 91/06333 | 5/1991 | PCT Int'l Appl. . |
| WO91/12197 | 8/1991 | PCT Int'l Appl. . |
| WO 91/12198 | 8/1991 | PCT Int'l Appl. . |
| 91/13689 | 9/1991 | PCT Int'l Appl. . |
| 92/00812 | 1/1992 | PCT Int'l Appl. . |
| 92/06727 | 4/1992 | PCT Int'l Appl. . |
| 141615 | 9/1990 | Taiwan . |
| 150946 | 2/1991 | Taiwan . |
| 1379508 | 12/1972 | United Kingdom . |
| 2064964 | 6/1981 | United Kingdom . |

Primary Examiner—Andres Kashnikow
Assistant Examiner—Philippe Derakshan
Attorney, Agent, or Firm—Darby & Darby

[57] ABSTRACT

The application describes a dispenser for manual discharge of a single dose of a flowable substance, comprising a casing (1) which has a nozzle (2) and a pair of shoulders (3) aside the nozzle. The nozzle (2) has a piston member (5) extending inwardly from an outlet opening (9), the piston member having at least one discharge channel. A container (10) of the substance to be discharged is mounted on the piston member (5), and a seal (12) is arranged across the container (10) to seal in all the substances to be discharged. The piston member (5) has a piercing member (8) which extends towards the seal (12), whereby on pressing the container (10) on to the piston member (5) the seal (12) is pierced to allow the contents of the container (10) to be expelled along the discharge channel and out through the outlet opening (9).

20 Claims, 1 Drawing Sheet

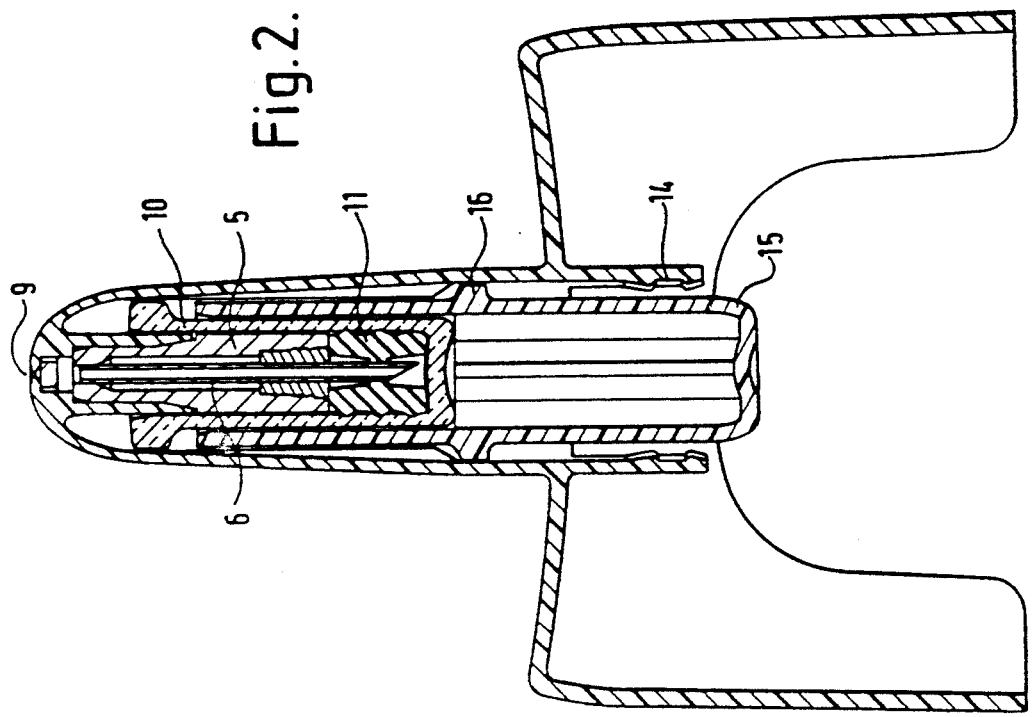
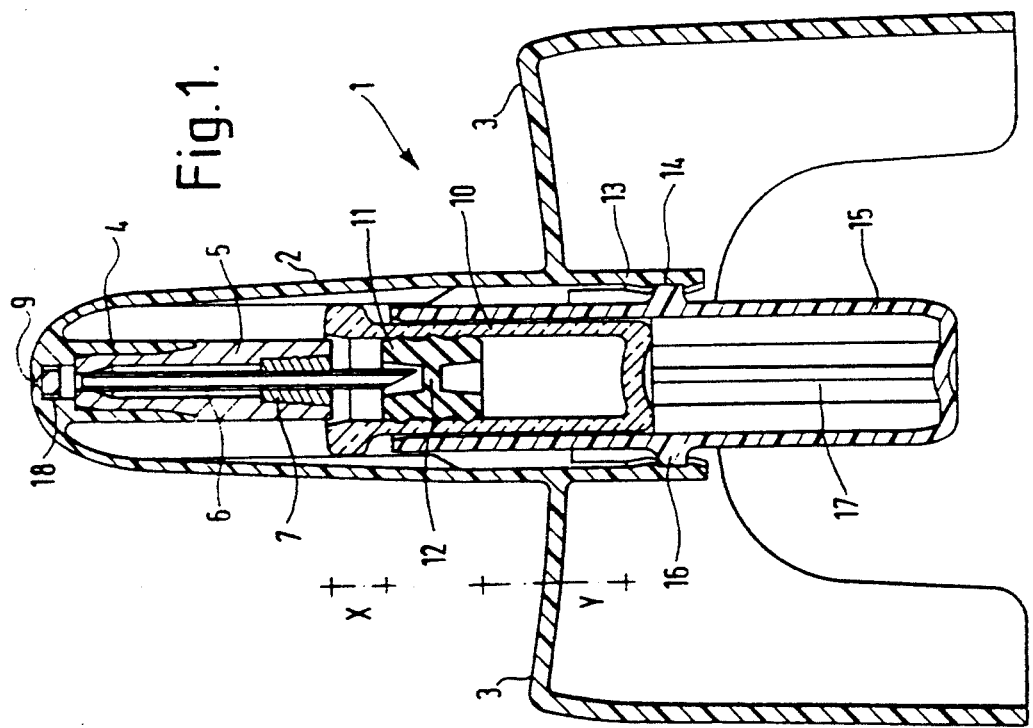

SINGLE DOSE DISPENSER HAVING A PIERCING MEMBER

BACKGROUND OF THE INVENTION

The invention relates to a unit-dose discharging device of the type in which a single cylinder containing one dose of a flowable substance to be discharged is moved manually relative to a piston in order to expel the contents of the cylinder through a nozzle opening in the piston. This device is particularly adapted for intranasal adminstration of a predetermined dose of a pharmaceutical substance in liquid form. The device is suited for the intranasal administration of the drug sumatriptan for use in the treatment of conditions associated with cephalic pain, such as cluster headache, chronic paroxysmal hemicrania, headache associated with vascular disorders, headache associated with substances or their withdrawal, tension headache, and in particular migraine.

U.S. Pat. No. 4946069—equivalent to European Patent Publication No. 0311863—describes this type of device. The device has a hollow casing with a nozzle extending from one end, the other end of the casing being open. A piston extends towards the body of the casing from the nozzle and a cylinder containing a dose of the substance to be discharged is mounted on the piston. The piston has at least one discharge channel along its length communicating with the nozzle outlet. On both sides of the nozzle, the casing has rounded shoulders on which two fingers of the user's hand can rest. The device is thus generally oval in plan view. Two opposite sides of the casing have recesses so that the thumb of the user's hand can extend across the shorter dimension of the casing, in contact with the cylinder.

Thus, to use the device, the user simply holds it in one hand with the nozzle at one nasal cavity and presses the container with his or her thumb. Since the volume of the container is known, since the container is filled with a predetermined amount of the substance, and since the pump stroke of the cylinder is defined by the device, a unit dose of the pharmaceutical substance can be reliably and easily administered. The device is disposable after use.

Although the device is relatively simply constructed and is easy to use, a disadvantage does arise from the simple construction. The disadvantage is that, since the discharge channel or channels through the piston communicate with the outside environment, the contents of the cylinder are not entirely closed off from the outside. There is therefore a possibility of loss of the contents of the cylinder over time through evaporation. There is also the problem of contamination, for example microbiological contamination, which is a particular disadvantage where pharmaceuticals are being dispensed. Thus, the device would also require hermetically sealed packaging, e.g. double foil blister packaging, which can make the pack large and cumbersome for the user to carry.

A solution to the problem of the open cylinder of the known device has been briefly mentioned by the proprietors of the above mentioned U.S. Pat. No. 4946069, namely Ing. Erich Pfeiffer GmbH & Co. KG, in U.S. Pat. No. 4921142—equivalent to European Patent Publication No. 218840. In these publications there is mentioned the possibility of the discharge channel being sealed by a membrane which is broken by the pressure inside the container when it is pushed onto the piston. In the equivalent German publication, DE-OS-3631341, there is also described the possibility of the membrane being broken by a penetrating element fitted in the container. However, since the seal is formed on the piston of the discharging device there remains the disadvantage that the container which holds the substance to be discharged can remain unsealed for a period of time before it is fitted onto the device. The potential for contamination of the contents of the container thus still remains.

Pfeiffer propose another solution in European Patent Publication No. 0388651. In this publication there is disclosed a device in which the cylinder has a central pin extending from its base along the central axis, the pin having a diameter slightly less than that of the central discharge channel of the piston. The pin, however, has a hollow flared end which, at least in theory, seals against the mouth of the discharge opening of the piston. Upon actuation by the user, the pin is forced into the discharge channel and the flared end is deformed inwardly, thereby allowing the contents of the cylinder to flow along the channel and out through the nozzle. In practice, it may be difficult to achieve a reliable seal with this arrangement, and the problem with respect to evaporation around the piston flanges is not wholly overcome. Again the container is not sealed for a time before it is fitted onto the discharge device.

In European Patent Publication No. 452728 (Coster) there is described similar type of discharge device which, like the above mentioned Pfeiffer proposal, has a membrane seal. The membrane is fitted immediately behind the nozzle opening and has a pre-formed slit which opens under a predetermined pressure.

A slightly different form of the device is described in European Patent Publication No. 407276 —(Valois) equivalent to Canadian Patent No. 2020425. In this device, the substance to be discharged is contained within the body of the device and is expelled by the user pressing a piston into the device. The substance, typically a powder, may be sealed off from the piston by means of a tearable partition and the piston can be formed with a penetrating member. Movement of the piston firstly increases pressure behind the partition and then the partition is broken by the penetrating member, the compressed air expelling the powder.

In a different art, syringes are known which have a membrane sealing the syringe barrel and a double ended discharge needle. In use, pressure on the plunger of the syringe moves the membrane towards the rear end of the needle, which then punctures the membrane, and further movement of the plunger discharges the contents U.S. Pat. No. 4017007 (Ciba-Geigy) describes a dispenser which includes a single dose container having a compressed air inlet opening and a closable discharge orifice. The container can either be mounted on a piston pump separately or the container and the pump can be combined in an integral container pump assembly. The valve means includes a breakable diaphragm which is located at the junction of the inlet opening of the container and the compressed air outlet of the pump. A pin is mounted on the forward face of the piston of the pump. During compression, when the front face of the piston reaches the end of its stroke, the diaphragm is ruptured by the pin and the compressed air surges into the interior of the container to thereby expel the product out through the discharge orifice.

International Patent Publications Nos. WO91/12197 and WO91/12198 (CP Packaging) describe unit dose assemblies consisting of compressible tubes, sealed by a thin wall, and closed by caps. In both cases, the cap has an inner spike and when the cap is pushed onto the tube the thin wall is punctured to allow the contents to be dispersed. In the first case, the contents are dispersed through the spike, which is hollow, onto an applicator pad on the cap. In the second case, the cap is removed to allow the contents of the tube to be expelled.

European Patent Publication No. 282338 (Unidec) discloses a liquid dispenser comprising a compressible container and an applicator with an internal spike. When the container is compressed, a membrane which seals the container is forced onto the spike by means of the pressure inside the container. The contents are then expelled through the applicator.

SUMMARY OF THE INVENTION

The object of the invention is to provide a discharge device of the type initially described, in which the container can be sealed in a reliable manner and can therefore be sterilised and remain free from contamination and evaporation losses. Also, unlike the earlier devices, it obviates the need to sterilize the whole device and provide secondary packaging.

Accordingly, the invention provides a unit-dose dispenser for manual discharge of a single dose of a flowable substance, comprising a casing which has a nozzle and two shoulders, one on either side of the nozzle, the nozzle having a piston member extending inwardly from an outlet opening, the piston member having at least one discharge channel, and a container of the substance to be discharged being mounted on the piston member, wherein a seal is arranged across the container to seal in all the substance to be discharged, and wherein the piston member has a piercing member which extends towards the seal, whereby on pressing the container on to the piston member the seal is pierced to allow the contents of the container to be expelled along the discharge channel and out through the outlet opening.

An advantage of the invention is that the container can be separately filled, sealed and sterilized and its sterility is maintained while it is fitted onto the dispenser before actuation occurs.

Advantageously, the seal is formed by a stopper which is movably engaged inside the container and has a central membrane which, in use, is pierced by the piercing member. The piercing member can be hollow, thereby forming the discharge channel of the piston.

The container or another member fitted thereto preferably engages on the inside of the casing, the engagement being released by a predetermined force which provides for efficient discharge of the substance in the container.

The substance is preferably a pharmaceutical substance, for example for the treatment of migraine, influenza, respiratory diseases or allergic rhinitis. It is, for example, sumatriptan. The discharge volume is preferably substantially 0.1 ml.

A preferred embodiment of the invention is described in detail below, by example only, with reference to the accompanying drawings:

BRIEF DESCRIPTION OF THE DRAWINGS

FIG. 1 is a sectional view of a dispensing device, prior to discharge of the contents of the cylinder; and
FIG. 2 is a view like FIG. 1 but after discharge.

DETAILED DESCRIPTION

The device illustrated in the Figures is similar to the device illustrated and described in detail in U.S. Pat. No. 4946069, the disclosure of which is incorporated herein by reference. The present description will not therefore describe in detail the features of the present devices which are common to the device of the said U.S. patent.

As shown in FIG. 1, the dispensing device comprising a casing 1 with a nozzle 2 and shoulders 3 either side of the nozzle. The casing 1 extends downwardly from the shoulders 3—which are rounded when viewed from above in FIGS. 1 and 2—and so is in the form of a flattened cylinder with one dimension (in the plane of the paper) being substantially greater than the other, perpendicular dimension. There are thumb-recesses on opposite sides of the casing across the narrower dimension, as in U.S. Pat. No. 4946069. The illustrated embodiment is designed for intranasal use and therefore the nozzle can be described as a nasal adaptor and will be so described below.

The nasal adaptor 2 is hollow and includes an internal cylindrical sleeve 4 extending towards the body of the casing. Piston member 5 is mounted in the sleeve 4 by means of a push fit. The piston 5 is hollow and mounted along its central axis is a piercing member or needle 6, here in the form of a hollow stainless steel needle. The needle 6 is fitted in an insert 7 which is then push fitted into the end of hollow piston 5. The needle communicates with an outlet opening 9 at the end of the nasal adaptor.

The device includes a single cylindrical container 10, which is mounted at the end of the piston 5 and is movable into the space between the wall of the nasal adaptor 2 and the piston 5 along the piston.

An annular rubber stopper 11 is fitted into the container 10, the stopper 11 including a central membrane 12. A series of annular rims on the outside of the stopper provide a good seal in the cylinder. The substance to be dispensed is wholly contained within the container 10 by the stopper 11; no substance is stored above the stopper as this would be in an unsterile environment.

In the illustrated embodiment, the nasal adaptor is extended inside the body of the casing to form an extension 13. The extension 13 can be formed by four spaced arms which together describe a cylindrical shape. The extension arms can flex outwardly. On the inside of the extension arms 13 are formed recesses 14. A separate cover 15 fits over the container 10 and an outer rim 16 of the cover clips into the recesses 14. Either the recesses 14 or rim 16 have rounded edges to allow for ease of engagement and disengagement after an initial resilient force has been overcome.

There is an interference fit between the container 10 and the container cover 15, internal webs 17 at the base of the container cover 15 limiting the extent to which the container extends into the container cover. The outlet opening 9 of the nasal adaptor is formed by an orifice of a relatively small diameter, for example 0.25 mm. The discharge channel, in this embodiment formed by the hollow needle, communicates with the outlet opening 9 by means of a conventional circular swirl chamber 18 formed at the end of the piston 5.

In use the device is actuated by the user pressing the container cover 15 with sufficient force to release the engagement of the rim 16 in recesses 14. Following this release the container 10 move along piston 5. This movement forces the needle 6 through the membrane 12 of the rubber stopper 11.

After the membrane has been pierced by the needle 6, the contents of the container can pass along the hollow needle, through swirl chamber 18 and be sprayed out through the outlet opening 9 at the end of nasal adaptor.

To ensure a fine spray from the nozzle, an adequate force must be applied during actuation. It should be noted that the relatively high force required initially to move the rim 16 of the container cover 15 out of the recesses 14 acts to build up a momentum for actuation and ensures a fine spray.

In the final position of the cylinder 8, seen in FIG. 2, the rubber stopper 11 is pushed to the bottom of the container by the piston 5 with the needle 6 extending almost to the bottom of the container. This ensures that most of the contents of the container are expelled. After use, the dispenser is disposed of. It is thus a "one-shot" unit dose disposable dispenser.

It should be explained that upon initial pressure on the container cover 15 both the container 10 and the stopper 11 move forward (distance X in FIG. 1) because of the internal pressure in the container, thus allowing the needle 6 to pierce the membrane. Continued forward movement of the container (distance Y in FIG. 1) forces the liquid in the container out through the needle. The pierced membrane 12 seals on the outside of the needle 6 to prevent liquid from being forced out other than through the hollow center of the needle.

It should be made clear that, although in the illustrated devices the casing has opposing recesses for the thumb of the user, in an alternative embodiment the container cover could be extended in both length and width to provide a larger area for the user to press. Thus, the container cover could be extended to form a sliding body fitting inside the casing. In such a case, the opposing apertures on the casing may be unnecessary, though this naturally depends upon the extent to which the sliding body extends out of the casing. A cap may be fitted onto the nasal adaptor to maintain its sterility before actuation. Alternatively, the device could be sealed within an airtight pack.

In the embodiment of FIGS. 1 and 2, the container can advantageously be made from glass, with advantages from the point of view of sterility and pharmaceutical stability, though it can of course be made from a plastics material. The casing, including the nasal adaptor, is moulded, for example from polypropylene, as is the container cover. The stopper can be made of chlorobutyl rubber and the membrane thickness can be approximately 1 mm, thereby providing good sealing against the outside of the needle. The membrane diameter may be 1.6 mm. The hollow needle can have an external diameter of 1 mm. Instead of being made of steel, the needle could be made of a relatively brittle plastics material, for example polycarbonate or polystyrene, or indeed from any other suitable material. The volume of the pharmaceutical substance to be administered may be 0.1 ml, though the container will tend to be filled to a volume of, for example, 0.12 ml to allow for the fact that, upon discharge, some of the substance will remain inside the device, rather than being sprayed out. Depending on the drug, the device may be modified to administer a different volume.

One advantage of the invention is that the container can be filled and sealed with the rubber stoppers and then sterilised as separate units, before being fitted into the casing. Upon fitting in the casing, the sterility of the container contents is maintained, by virtue of the seal.

What we claim is:

1. A unit-dose dispenser for manual discharge of a single dose of a flowable substance in the form of a spray, comprising a casing which has a nozzle and two shoulders, one on either side of this nozzle, the nozzle having a piston member extending inwardly from and outlet opening, the piston member having at least one discharge channel, a container of the substance to be discharged being operatively positioned with respect to the piston member, and a seal being arranged across the container to seal in all the substance to be discharged, the piston member having a piercing member which extends towards the seal, whereby on pressing the container onto the piston member the seal is pierced to allow the contents of the container to be expelled along the discharge channel and out through the outlet opening in the form of the spray.

2. A dispenser according to claim 1, wherein the seal is formed by a stopper which is movably engaged inside the container and has a central membrane which, in use, is pierced by the piercing member.

3. A dispenser according to claim 2, wherein the piercing member is hollow, thereby forming the discharge channel of the piston.

4. A dispenser according to claim 3, wherein the piercing member extends along the axis of the piston member to the outlet opening.

5. A dispenser according to claim 4, wherein the piercing member is a steel needle.

6. A dispenser according to claim 1, wherein the container engages on the inside of the casing, the engagement being released by a predetermined force which provides for efficient discharge of the substance in the container.

7. A dispenser according to claim 1, wherein the container contains a pharmaceutical substance.

8. A dispenser according to claim 7, wherein the substance is for the treatment of migraine, influenza, respiratory diseases or allergic rhinitis.

9. A dispenser according to claim 7, wherein the pharmaceutical substance is sumatriptan.

10. A dispenser according to claim 7, wherein the discharge volume of the substance is substantially 0.1 ml.

11. A unit-dose dispenser for manual discharge of a single dose of a flowable substance in the form of a spray, comprising a casing which contains a nozzle and two shoulders, one on either side of the nozzle, the nozzle incorporating a piston member extending inwardly from an outlet opening, the piston member having at least one discharge channel, and a container of the substance to be discharged being operatively positioned with respect to the piston member and within the casing, wherein a seal is arranged across the container to seal in all the substance to be discharged, and wherein the piston member has a piercing member which extends towards the seal, whereby on pressing the container onto the piston member the seal is pierced to allow the contents of the container to be expelled along the discharge channel and out through the outlet opening in the form of a spray.

12. A dispenser according to claim 11, wherein the seal is formed by a stopper which is movably engaged inside the container and has a central membrane which, in use, is pierced by the piercing member.

13. A dispenser according to claim 12, wherein the piercing member is hollow, thereby forming the discharge channel of the piston.

14. A dispenser according to claim 13, wherein the piercing member extends along the axis of the piston member to the outlet opening.

15. A dispenser according to claim 14, wherein the piercing member is a steel needle.

16. A dispenser according to claim 11, wherein the container engages on the inside of the casing, the engagement being released by a predetermined force which provides for efficient discharge of the substance in the container.

17. A dispenser according to claim 11, wherein the container contains a pharmaceutical substance.

18. A dispenser according to claim 17, wherein the substance is for the treatment of one of migraine, influenza, respiratory disease and allergic rhinitis.

19. A dispenser according to claim 17, wherein the pharmaceutical substance is sumatriptan.

20. A dispenser according to claim 17, wherein the discharge volume of the substance is substantially 0.1 ml.

* * * * *